United States Patent
Eshita

(10) Patent No.: US 6,899,865 B2
(45) Date of Patent: May 31, 2005

(54) ORAL COMPOSITION COMPRISING WATER AND CYCLIC CARBONATE IN TWO PHASE STATE

(75) Inventor: Yoshiyuki Eshita, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/309,144

(22) Filed: Dec. 4, 2002

(65) Prior Publication Data

US 2003/0152524 A1 Aug. 14, 2003

(30) Foreign Application Priority Data

Dec. 4, 2001 (JP) .......................................... 2001-369635
Oct. 11, 2002 (JP) .......................................... 2002-299694

(51) Int. Cl.$^7$ .............................. A61K 7/16; A61K 7/20
(52) U.S. Cl. .............................. 424/49; 424/52; 424/54; 424/56; 424/57; 252/79.1; 252/79.3; 252/79.4; 252/364; 433/215; 510/109; 510/397; 510/417
(58) Field of Search .................. 424/49–58; 252/79.1, 252/79.3, 79.4, 364; 433/216; 510/109, 397, 417; 404/49–58

(56) References Cited

U.S. PATENT DOCUMENTS

| | | | | |
|---|---|---|---|---|
| 2,894,957 A | * | 7/1959 | Von Dohlen et al. | ....... 549/230 |
| 3,616,803 A | | 11/1971 | Menkart et al. | |
| 4,474,750 A | * | 10/1984 | Gaffar et al. | .................. 424/49 |
| 4,606,913 A | * | 8/1986 | Aronson et al. | ............... 424/59 |
| 4,714,670 A | * | 12/1987 | Amariti et al. | ............. 430/331 |
| 5,198,220 A | * | 3/1993 | Damani | ....................... 424/426 |
| 5,478,365 A | * | 12/1995 | Nikanjam et al. | ............ 44/280 |
| 5,747,058 A | * | 5/1998 | Tipton et al. | ................ 424/423 |
| 5,885,552 A | * | 3/1999 | Causton | ........................ 424/49 |
| 5,962,699 A | | 10/1999 | Marquis et al. | |
| 5,968,542 A | * | 10/1999 | Tipton | ......................... 424/423 |
| 6,238,648 B1 | * | 5/2001 | Leusch et al. | ................. 424/49 |
| 6,342,205 B1 | | 1/2002 | Niemi et al. | |
| 6,350,438 B1 | * | 2/2002 | Witt et al. | .................... 424/53 |
| 6,544,942 B1 | | 4/2003 | Smith et al. | |

FOREIGN PATENT DOCUMENTS

| | | |
|---|---|---|
| JP | 1-104004 | 4/1989 |
| JP | 2000-239135 | 5/2000 |
| JP | 2000-229824 | 8/2000 |

OTHER PUBLICATIONS

Merck Index, $12^{12}$ Edition, Merck & Co., Inc., pp. 1478 and 1479 (1996).*

* cited by examiner

*Primary Examiner*—Frederick F. Krass
(74) *Attorney, Agent, or Firm*—Oblon, Spivak, McClelland, Maier & Neustadt, P.C.

(57) ABSTRACT

An oral composition comprises water and a cyclic carbonate compound in a certain ratio. In this case, the ratio of the water and the cyclic carbonate compound is such that when the water and the cyclic carbonate compound are mixed together the mixture goes into a 2-phase state. Moreover, the oral composition may further comprise a polyol, and in this case the ratio of the water, the cyclic carbonate compound and the polyol is such that when the water, the cyclic carbonate compound and the polyol are mixed together the mixture goes into a 2-phase state. The oral composition has an excellent effect of removing accumulations on dental surfaces or between teeth through a physico-chemical action, rather than relying purely on a mechanical action.

21 Claims, No Drawings

ORAL COMPOSITION COMPRISING WATER AND CYCLIC CARBONATE IN TWO PHASE STATE

BACKGROUND OF THE INVENTION

1. Field of the Invention

The present invention relates to an oral composition having the improved effect of physico-chemically removing accumulations on dental surfaces or between teeth.

2. Description of the Related Art

Conventionally, the removal of accumulations such as stain, dental plaque, food debris and tobacco tar adhered to or deposited on dental surfaces or between teeth is carried out predominantly by the mechanical action of an abrasive comprised in an oral composition such as a toothpaste. As the abrasive, one for which surface abrasion is low is selected, for example an inorganic powder of calcium hydrogenphosphate dihydrate, calcium carbonate, silicic anhydride or the like is used.

However, there has been a problem that when trying to remove accumulations on dental surfaces with an oral composition comprising such an abrasive, it is not possible to completely prevent abrasion of soft parts of the teeth such as the root surface.

Consequently, the following have been proposed as oral compositions comprising a component that can remove accumulations such as stain, dental plaque, food debris and tobacco tar adhered to or deposited on dental surfaces or between teeth not merely mechanically but rather through a physico-chemical action: (1) an oral composition comprising an aliphatic ester having 7 to 11 carbon atoms in total (Japanese Patent Application Laid-open No. 1-104004); (2) an oral composition comprising an alcohol that has a phenyl group or a phenoxy group (Japanese Patent Application Laid-open No. 2000-229824); (3) an oral composition comprising an isopropyl carboxylate and a water-soluble polyphosphate (Japanese Patent Application Laid-open No. 2000-239135); and so on.

However, in the case of the oral composition disclosed in Japanese Patent Application Laid-open No. 1-104004, an aliphatic ester having 7 to 11 carbon atoms in total is used as a component having an effect of removing tobacco tar and the like, but there is a problem that the cleaning ability is low and accumulations cannot be removed sufficiently.

Moreover, in the case of the oral composition disclosed in Japanese Patent Application Laid-open No. 2000-229824, an alcohol that has a phenyl group or a phenoxy group is used as a component having an effect of removing tobacco tar and the like, but because of the presence of a phenyl group or a phenoxy group, such alcohols irritate the oral mucosa, and thus are not necessarily desirable as a component of an oral composition.

Moreover, in the case of the oral composition disclosed in Japanese Patent Application Laid-open No. 2000-239135, an isopropyl carboxylate and a water-soluble polyphosphate are used as components having an effect of removing tobacco tar and the like, but there is a problem that the cleaning ability is low and accumulations cannot be removed sufficiently.

SUMMARY OF THE INVENTION

It is an object of the present invention to provide an oral composition that has an excellent effect of removing accumulations on dental surfaces or between teeth through a physico-chemical action, rather than relying merely on a mechanical action (e.g. brushing).

The present inventors have accomplished the present invention after discovering that an oral composition comprising water and a cyclic carbonate (cyclic carbonic ester) compound in a ratio such that when the water and the cyclic carbonate are mixed together the mixture goes into a 2-phase state is capable of effectively removing accumulations such as stain and dental plaque on dental surfaces and between teeth.

The present invention thus provides an oral composition, comprising undermentioned component (A) and component (B):

(A) water; and (B) cyclic carbonate compound;

wherein the mixing ratio of component (A) and component (B) is such that when component (A) and component (B) are mixed together the mixture goes into a 2-phase state.

DESCRIPTION OF THE PREFERRED EMBODIMENTS

The oral composition of the present invention comprises as essential components a component (A), which is water, and a component (B), which is cyclic carbonate compound. The cyclic carbonate compound (component (B)) is a component that dissolves accumulations adhered to dental surfaces or between teeth, or else penetrates between dental surface and accumulations, thus loosens binding of accumulations and hence making the accumulations easy to remove. Suitable cyclic carbonate compound include, but are not limited to, ethylene carbonate and propylene carbonate.

A cyclic carbonate compound, for example, propylene carbonate has a polar group that makes dissolving of tobacco tar easy, and also has water solubility of 1 to 10%. If there is a little amount of water, then the propylene carbonate and the water can thus be made to be in a 2-phase state, with there being no mutual dissolution between the propylene carbonate and the water, and hence the propylene carbonate can be made to function effectively as a solvent that dissolves tobacco tar. Moreover, if rinsing with water is carried out in a state in which the propylene carbonate has dissolved tobacco tar and so on, then the tobacco tar that has been dissolved by the propylene carbonate dissolves in the water as is along with the propylene carbonate and is washed away; the removal of tobacco tar by the propylene carbonate can thus be achieved effectively.

Conversely, if the cyclic carbonate compound is in a state dissolved in the water, then the function of the cyclic carbonate compound as a solvent that dissolves or lifts accumulations becomes weaker, and hence the accumulations removal efficiency is decreased.

With the oral composition of the present invention, it is thus necessary for the mixture of the water (component (A)) and the cyclic carbonate compound (component (B)) to be in a 2-phase state. The mixing ratio of the water (component (A)) and the cyclic carbonate compound (component (B)) in the oral composition, while depending on the amount of moisture in the oral composition, the type of the cyclic carbonate compound and so on, is thus a ratio such that when the water (component (A)) and the cyclic carbonate compound (component (B)) are mixed together the mixture goes into a 2-phase state.

Here, the 2-phase state exhibited by the mixture when the water (component (A)) and the cyclic carbonate compound (component (B)) are mixed together means a state other than the state in which the mixture of the water and the cyclic carbonate compound form a single phase by mutually dissolved. Specifically, the 2-phase state means (1) a state in which the mixture is separated into two transparent phases, (2) a state in which the mixture is cloudy and not separated, (3) a state in which the mixture is separated into a cloudy layer and a transparent layer, or the like.

Moreover, in addition to the water (component (A)) and the cyclic carbonate compound (component (B)), it is preferable to also include a polyol that does not mutually dissolve with the cyclic carbonate compound (component (B)) as a component (C) in the oral composition of the present invention. By including such a polyol, it becomes easier for the water (component (A)) and the cyclic carbonate compound (component (B)) to go into 2-phase state. The mixing ratio of the water (component (A)), the cyclic carbonate compound (component (B)) and the polyol (component (C)) in the oral composition, while depending on the amount of moisture in the oral composition, the types of the cyclic carbonate compound and the polyol and so on, is thus a ratio such that when the water (component (A)), the cyclic carbonate compound (component (B)) and the polyol (component (C)) are mixed together the mixture goes into a 2-phase state.

Examples of the polyol include propylene glycol, glycerol, sorbitol, and xylitol. Of these, glycerol, sorbitol, xylitol and the like are preferable. Note that so long as the mixture goes into a 2-phase state when the water (component (A)), the cyclic carbonate compound (component (B)) and the polyol (component (C)) are mixed together, one or more selected from the group consisting of propylene glycol, glycerol, sorbitol and xylitol can be included in the oral composition. These polyols also act as humectants.

Here, the 2-phase state exhibited by the mixture when the water (component (A)), the cyclic carbonate compound (component (B)) and the polyol (component (C)) are mixed together means a state other than the state in which the mixture of the water, the cyclic carbonate compound and the polyol form a single phase by mutually dissolved. Specifically, the 2-phase state means (1) a state in which the mixture is separated into two transparent phases, (2) a state in which the mixture is cloudy and not separated, or (3) a state in which the mixture is separated into a cloudy layer and a transparent layer, or the like.

In accordance with the usage and formulation, various additives commonly used in conventional oral compositions can be included in the oral composition of the present invention. For example, abrasives, binders, humectants, surfactants, sweeteners, flavors, pH regulators and so on can be included in ranges such that the effects of the present invention are not impaired.

Examples of abrasives include calcium hydrogenphosphate dihydrate, calcium triphosphate, calcium carbonate, calcium pyrophosphate, aluminum hydroxide, alumina, silicic anhydride, aluminum silicate, zeolite, insoluble sodium metaphosphate, magnesium triphosphate, magnesium carbonate, calcium sulfate, bentonite, zirconium silicate, hydroxyapatite, and polymethyl methacrylate and other synthetic resins. One of these can be used, or two or more can be used mixed together.

Note that in the case of including an abrasive in the oral composition of the present invention, because the oral composition of the present invention comprises as an essential component a cyclic carbonate compound that can efficiently remove accumulations on tooth surfaces through a physico-chemical action, the amount of the abrasive used can be less than normal (i.e., less than the amount used when the abrasive is included in an oral composition that removes accumulations on tooth surfaces predominantly through a mechanical action).

Moreover, examples of binders include cellulose derivatives such as sodium carboxymethyl cellulose, and hydroxyethyl cellulose; alginic acid derivatives such as sodium alginate, and propylene glycol alginate; gums such as carrageenan, xanthan gum, Duran gum, tragacanth gum, and karaya gum; synthetic binders such as polyvinyl alcohol, sodium polyacrylate, and carboxyvinyl polymers; and inorganic binders such as silica gel, bee gum, and laponite. One of these can be used, or two or more can be used mixed together.

Examples of humectants include glycerol, sorbitol, propylene glycol, and xylitol as mentioned earlier; and also polyethylene glycol, maltitol, and lactitol. One of these can be used, or two or more can be used mixed together.

Examples of surfactants include anionic surfactants such as sodium lauryl sulfate, sodium myristyl sulfate, sodium lauroyl sarcosine, sodium lauroyl methyltaurine, and sodium cocoyl ethyl ester sulfonate; nonionic surfactants such as polyglceryl laurate, and polyglceryl myristate; and amphoteric surfactants such as betaine type surfactants. One of these can be used, or two or more can be used mixed together.

Examples of flavors include menthol, anethole, carvone, eugenol, limonene, n-decyl alcohol, citronellol, $\alpha$-terpineol, cineole, linalool, ethyl linalool, vanillin, thymol, peppermint oil, spearmint oil, wintergreen oil, clove oil, and eucalyptus oil. One of these can be used, or two or more can be used mixed together.

Examples of sweeteners include Sodium saccharin, stevioside, glycyrrhizin, perillartine, and somatin. One of these can be used, or two or more can be used mixed together.

Examples of pH regulators include acids such as acetic acid, citric acid, succinic acid, tartaric acid, adipic acid, fumaric acid, malic acid, orthophosphoric acid, metaphosphoric acid, polyphosphoric acid, and carbonic acid, and also alkali metal salts thereof. One of these can be used, or two or more can be used mixed together.

Moreover, with the present invention, one or more publicly known active ingredients such as the following can be included in the oral composition: cationic microbicides such as chlorhexadine, benzethonium chloride, benzalkonium chloride, cetylpyridinium chloride, and dequalinium chloride; phenolic compounds such as triclosan, hinokitiol, and biozole; enzymes such as dextranase, mutanase, lysozyme, amylase, protease, lytic enzymes, and superoxide dismutase; vitamins such as vitamin E; and vitamin B6; alkali metal monofluorophosphates such as sodium monofluorophosphate, and potassium monofluorophosphate; fluorides such as sodium fluoride, and stannous fluoride; tranexamic acid; epsilon-amino-caproic acid; aluminum chlorohydroxyl allantoinate; dihydrocholesterol; glycyrrhizinic acid; glycyrrhetinic acid; Bisabolol; glycerophosphates; chlorophyll; sodium chloride; and water-soluble inorganic phosphates.

With the exception of comprising a cyclic carbonate compound, the oral composition of the present invention can be made to have the same constitution as a publicly known oral composition. Moreover, the oral composition of the present invention can be applied with the same usages and formulations as conventional oral compositions. For example, the oral composition of the present invention can be used as a toothpaste, a liquid tooth cleaner, a transparent gel-type tooth cleaner, a mouthwash, a liniment or the like; nevertheless, from the standpoint of removing accumulations on dental surfaces or between teeth predominantly by a physico-chemical action, it is preferable for the usage/formulation to be, for example, a teeth cleaning agent that comprises a little amount of abrasive, or a mouthwash that does not comprise abrasive.

EXAMPLES

Example 1

Oral compositions of Experiments 1 to 11 having the compositions shown in Tables 1 and 2 were prepared, and the state of dissolution (mutual solubility) between the water and the cyclic carbonate compound (and the polyol where used), the cleaning ability (%), and the feeling of irritation were investigated for each of the oral compositions as described below. The results obtained are shown in Tables 1 and 2.

(Mutual Solubility)

8 ml of a mixture of the components (A) and (B) or the components (A) to (C) was put into a 10 ml lidded test tube, the test tube was shaken by hand for 10 seconds, and then the state after leaving for 1 day was observed, with it being investigated whether the mixture was uniformly dissolved, or whether the mixture was separated into two phases.

(Cleaning Ability (%))

Cleaning tests were carried out using acrylic plates on which tobacco tar had been adsorbed as a tooth accumulations model. Specifically, acrylic plates that had been subjected to abrasive blasting were left in a desiccator filled with tobacco smoke, thus adsorbing tobacco tar onto the surfaces of the acrylic plates. Next, the acrylic plates on which the tobacco tar had been adsorbed were taken out of the desiccator, and were brushed lightly in ion exchanged water to remove excess tobacco tar adsorbate, thus obtaining acrylic plates for the cleaning tests.

The acrylic plates for the cleaning tests thus produced were brushed lightly with a toothbrush in the oral compositions (cleaning liquids) of Experiments 1 to 11 having the compositions (wt %) shown in Tables 1 and 2, and were then rinsed with water, thus cleaning the surfaces on which tobacco tar had been adsorbed. The color difference $\Delta E_0$ (CIE Lab) between before and after adsorbing the tobacco tar, and the color difference $\Delta E_1$ (CIE Lab) between before and after cleaning were each measured for each of the acrylic plates, and the cleaning ability was calculated using the undermentioned formula. Here, the higher the cleaning ability, the better the cleaning ability.

Cleaning ability (%)=($\Delta E_1/\Delta E_0$)×100

(Evaluation of Feeling of Irritation)

The feeling of irritation was evaluated for each of the oral compositions, with the evaluation being 'no' in the case that irritation in the oral cavity and on the lips was not felt, and 'yes' in the case that irritation in the oral cavity and on the lips was felt.

TABLE 1

| Component name | Experiment (wt %) | | | | | |
|---|---|---|---|---|---|---|
|  | 1 | 2 | 3 | 4 | 5 | 6 |
| Propylene carbonate | 10 | 15 | 20 | — | — | — |
| Ethylene carbonate | — | — | — | 50 | 40 | 37.5 |
| Ion exchanged water | 90 | 85 | 80 | 50 | 40 | 37.5 |
| Glycerol | — | — | — | — | 20 | 25 |
| Sorbitol 70% solution | — | — | — | — | — | — |
| Xylitol | — | — | — | — | — | — |
| Total | 100 | 100 | 100 | 100 | 100 | 100 |
| Mutual solubility | Dissolution | Dissolution | 2-phases | Dissolution | Dissolution | 2-phases |
| Cleaning ability (%) | 20 | 25 | 95 | 15 | 20 | 95 |
| Feeling of irritation | No | No | No | No | No | No |

TABLE 2

| Component name | Experiment (wt %) | | | | |
|---|---|---|---|---|---|
|  | 7 | 8 | 9 | 10 | 11 |
| Propylene carbonate | — | — | — | — | — |
| Ethylene carbonate | 45 | 40 | 37.5 | 40 | 37.5 |
| Ion exchanged water | 45 | 40 | 37.5 | 48 | 47.5 |
| Glycerol | — | — | — | — | — |
| Sorbitol 70% solution | 10 | 20 | 25 | — | — |
| Xylitol | — | — | — | 12 | 15 |
| Total | 100 | 100 | 100 | 100 | 100 |
| Mutual solubility | Dissolution | 2-phases | 2-phases | Dissolution | 2-phases |
| Cleaning ability (%) | 20 | 95 | 95 | 20 | 95 |
| Feeling of irritation | No | No | No | No | No |

It can be seen from Tables 1 and 2 that, depending on the mixing ratio of the water, the propylene carbonate or ethylene carbonate, and if required a polyol selected from glycerol, sorbitol and xylitol, there are cases in which mutual dissolution occurs, and cases in which the mixture goes into two phases.

In the case that the mixture constituting the oral composition underwent mutual dissolution, for example, in the case that the composition was 15 wt % of propylene carbonate and 85 wt % of water (Experiment 2), a low cleaning ability of 25% was exhibited. It is thought that this is because the mutual solubility between the propylene carbonate and the water is stronger than the affinity of the propylene carbonate to the tobacco tar, and hence the majority of the propylene carbonate in the oral composition is present in a state mutually dissolved with the water, and as a result the function of the propylene carbonate as a solvent for dissolving the tobacco tar is greatly reduced.

In the case that the mixture went into two phases, for example in the case that the composition was 20 wt % of propylene carbonate and 80 wt % of water (Experiment 3), because the propylene carbonate and the water in the oral composition went into a 2-phase state, the propylene carbonate could function effectively as a solvent for dissolving the tobacco tar. Moreover, if rinsing with water is carried out in a state in which the propylene carbonate has dissolved the tobacco tar and so on, then the tobacco tar that has been dissolved by the propylene carbonate is dissolved as is in the water along with the propylene carbonate and is washed away, and hence the removal of the tobacco tar by the propylene carbonate is achieved effectively, and as a result the cleaning ability was a high value of 95%.

Examples 2 and 3 Comparative Examples 1 to 3

The state of dissolution (mutual solubility) between the water and the cyclic carbonate compound (and the polyol where used), the cleaning ability (cleaning ability (%)), and the feeling of irritation were investigated as in Example 1 for oral compositions (cleaning liquids) of Examples 2 and 3 and Comparative Examples 1 to 3 having the compositions (wt %) shown in Table 3. The results obtained are shown in Table 3.

TABLE 3

|  | Example | | Comparative Example | | (wt %) |
| --- | --- | --- | --- | --- | --- |
| Component name | 2 | 3 | 1 | 2 | 3 |
| Propylene carbonate | 22 | — | — | — | — |
| Ethylene carbonate | — | 10 | — | — | — |
| Isopropyl myristate | — | — | 2 | — | — |
| Tetrasodium pyrophosphate | — | — | 3 | — | — |
| Butyl butyrate | — | — | — | 1 | — |
| Phenyl ethyl alcohol | — | — | — | — | 2 |
| Sorbitol | — | 63 | — | — | — |
| Ion exchanged water | 78 | 27 | 95 | 99 | 98 |
| Total | 100 | 100 | 100 | 100 | 100 |
| Mutual solubility | 2-phases | 20 phases | 20 phases | 20 phases | 20 phases |
| Cleaning ability (%) | 95 | 90 | 25 | 20 | 90 |
| Feeling of irritation | No | No | No | No | Yes |

As shown in Table 3, with the oral composition of Example 2, 22 wt % of a cyclic carbonate compound (propylene carbonate) was used, and the ratio of the propylene carbonate and the water was such that the mixture went into two phases; a good cleaning ability was thus exhibited, and moreover there were no problems with regard to a feeling of irritation; likewise for Example 3.

In contrast, with Comparative Examples 1 and 2, a cyclic carbonate compound was not included, and hence a poor cleaning ability was exhibited, and with Comparative Example 3, phenyl ethyl alcohol was included, and hence a good cleaning ability was exhibited, but there was irritation.

Example 4 Comparative Example 4

Toothpastes of the compositions shown in Table 4 were prepared, and the cleaning ability and the feeling of irritation were evaluated. The results are shown in Table 4.

TABLE 4

|  | Component name | Example 4 | (wt %) Comparative Example 4 |
| --- | --- | --- | --- |
| 1 | Silicic anhydride | 21.0 | 21.0 |
| 2 | Sodium lauryl sulfate | 1.5 | 1.5 |
| 3 | Titanium dioxide | 1.0 | 1.0 |
| 4 | Sodium Carboxymethyl cellulose | 1.0 | 1.0 |
| 5 | 70% sorbitol | 49.0 | 27.0 |
| 6 | Propylene glycol | — | 22.0 |
| 7 | Sodium fluoride | 0.2 | 0.2 |
| 8 | Sodium saccharin | 0.2 | 0.2 |
| 9 | Flavor | 1.0 | 1.0 |
| 10 | Propylene carbonate | 10.0 | 10.0 |
| 11 | Ion exchanged water | 15.1 | 15.1 |
|  | Total | 100.0 | 100.0 |
|  | Cleaning ability (%) | 98 | 45 |
|  | Feeling of irritation | No | No |

As shown in Table 4, the oral composition of Example 4 comprised 49.0 wt % of 70% sorbitol and 10.0 wt % of propylene carbonate, and this mixing ratio was such that the mixture of the cyclic carbonate compound, the polyol and the water went into a 2-phase state; a good cleaning ability was thus exhibited, and moreover there was no feeling of irritation. In contrast, with Comparative Example 4, the oral composition comprised 70% sorbitol, propylene glycol and propylene carbonate, but the cyclic carbonate compound, the polyol and the water were in a mutually dissolved state, and hence, although there was no feeling of irritation, a poor cleaning ability was exhibited.

Example 5

A toothpaste of the composition shown in Table 5 was manufactured using a normal method. The undermentioned toothpaste comprised 28.08 wt % of water, 30 wt % of 70% sorbitol, 10 wt % of xylitol, 3 wt % of propylene glycol, and 10 wt % of propylene carbonate; this mixing ratio was such that the mixture of the water, the 70% sorbitol, the xylitol, the propylene glycol and the propylene carbonate went into a 2-phase state. The toothpaste obtained was thus able to remove accumulations on dental surfaces more easily than a toothpaste that comprised water instead of the propylene carbonate (and was thus in a dissolved state).

TABLE 5

|  | Component name | wt % |
| --- | --- | --- |
| 1 | Silicic anhydride | 10.0 |
| 2 | Titanium dioxide | 0.5 |
| 3 | Sodium carboxymethyl cellulose | 1.0 |
| 4 | Carrageenan | 0.2 |
| 5 | Sodium lauryl sulfate | 1.0 |
| 6 | 70% sorbitol | 30.0 |
| 7 | Xylitol | 10.0 |
| 8 | Propylene glycol | 3.0 |
| 9 | Methylparaben | 0.02 |
| 10 | Sodium saccharin | 0.2 |
| 11 | Flavor | 1.0 |
| 12 | Tetrasodium pyrophosphate | 5.0 |
| 13 | Propylene carbonate | 10.0 |
| 14 | Ion exchanged water | 28.08 |
|  | Total | 100.0 |

Example 6

A toothpaste of the composition shown in Table 6 was manufactured using a normal method. The undermentioned toothpaste comprised 20.3 wt % of water, 50 wt % of 70% sorbitol, 8 wt % propylene carbonate, and 2 wt % of ethylene carbonate; this mixing ratio was such that the mixture of the water, the 70% sorbitol, the propylene carbonate and the ethylene carbonate went into a 2-phase state. The toooth-paste obtained was thus able to remove accumulations on dental surfaces or between teeth more easily than a toothpaste that comprised water instead of the ethylene carbonate and the propylene carbonate (and was thus in a dissolved state).

TABLE 6

|   | Component name | wt % |
|---|---|---|
| 1 | Silicic anhydride | 10.0 |
| 2 | Titanium dioxide | 0.5 |
| 3 | Hydroxyethyl cellulose | 1.0 |
| 4 | Sodium lauryl sulfate | 1.0 |
| 5 | 70% sorbitol | 50.0 |
| 6 | Polyethylene glycol | 5.0 |
| 7 | Sodium saccharin | 0.2 |
| 8 | Flavor | 1.0 |
| 9 | Sodium malate | 1.0 |
| 10 | Propylene carbonate | 8.0 |
| 11 | Ethylene carbonate | 2.0 |
| 12 | Ion exchanged water | 20.3 |
|   | Total | 100.0 |

Example 7

A mouthwash of the composition shown in Table 7 was manufactured using a normal method. The undermentioned mouthwash comprised 61.74 wt % of water, 12 wt % of glycerol, and 20 wt % of propylene carbonate; this mixing ratio was such that the mixture of the water, the glycerol and the propylene carbonate went into a 2-phase state. The mouthwash obtained was thus able to remove accumulations on tooth surfaces or between teeth more easily than a mouthwash that comprised water instead of the propylene carbonate (and was thus in a dissolved state).

TABLE 7

|   | Component name | wt % |
|---|---|---|
| 1 | Glycerol | 12.0 |
| 2 | Sodium saccharin | 0.01 |
| 3 | Sodium lauryl sulfate | 1.0 |
| 4 | Ethylparaben | 0.05 |
| 5 | Tea tree oil | 0.05 |
| 6 | Flavor | 0.15 |
| 7 | Tetrasodium pyrophosphate | 4.0 |
| 8 | Citric acid | 1.0 |
| 9 | Propylene carbonate | 20.0 |
| 10 | Ion exchanged water | 61.74 |
|   | Total | 100.0 |

As described above, the oral composition of the present invention is capable of effectively removing accumulations such as stain and dental plaque on dental surfaces and between teeth through a physico-chemical action, and cleaning even parts inside the oral cavity that a brush does not reach. The chemical cleaning effect inside the oral cavity can thus be markedly improved, and the effect of whitening/beautifying dental surfaces and between teeth can be increased.

The entire disclosures of the specifications, summaries and claims of Japanese Patent Applications No. 2001-369635 filed on Dec. 4, 2001 and No. 2002-299694 filed on Oct. 11, 2002 are hereby incorporated by reference.

What is claimed as new and is intended to be secured by Letters Patent is:

1. An oral composition, comprising component (A) and component (B):

(A) water;

(B) at least one cyclic alkylene carbonate compound; and a flavor selected from the group consisting of menthol, anethole, carvone, eugenol, limonene, n-decyl alcohol, citronellol, α-terpineol, cineole, linalool, ethyl linalool, vanillin, thymol, peppermint oil, spearmint oil, wintergreen oil, clove oil, eucalyptus oil and mixtures thereof;

wherein said component (A) and said component (B) are present at a wt. % ratio at which component (A) and component (B) exist in a 2-phase state.

2. The oral composition according to claim 1, further comprising component (C):

(C) at least one polyol humectant.

3. The oral composition of claim 1, wherein component (B) is propylene carbonate.

4. The oral composition of claim 1, wherein component (B) is ethylene carbonate.

5. The oral composition of claim 2, wherein component (C) does not mutually dissolve with component (B).

6. The oral composition of claim 2, wherein component (C) is selected from the group consisting of propylene glycol, glycerol, sorbitol, xylitol and mixtures thereof.

7. The oral composition of claim 1, further comprising at least one additive selected from the group consisting of an abrasive, a binder, a humectant, a surfactant, a sweetener, a pH regulator and mixtures thereof.

8. The oral composition of claim 1, further comprising a sweetener selected from the group consisting of sodium saccharin, stevioside, glycyrrhizin, perillartine, somatin and mixtures thereof.

9. The oral composition of claim 1, wherein said component (A) and said component (B) are present in a ratio of from 8:2 to 1:1.

10. The oral composition of claim 1, wherein said component (A) and said component (B) are present in a ratio of 1:1.

11. The oral composition of claim 2, wherein the ratio of (component (A)+component (C)) and component (B) is from 9:1 to 7/5:1.

12. The oral composition of claim 1, which is an oral care composition which further comprises an oral care agent.

13. The oral composition of claim 1, wherein said component (B) has a water solubility of 1 to 10%.

14. An oral composition, comprising component (A) and component (B):

(A) water;

(B) at least one cyclic alkylene carbonate compound; and a sweetener selected from the group consisting of sodium saccharin, stevioside, glycyrrhizin, perillartine, somatin and mixtures thereof;

wherein said component (A) and said component (B) are present at a wt. % ratio at which component (A) and component (B) exist in a 2-phase state.

15. The oral composition according to claim 14, further comprising component (C):

(C) at least one polyol humectant.

16. The oral composition of claim 14, wherein component (B) is propylene carbonate or ethylene carbonate.

17. The oral composition of claim 15, wherein component (C) does not mutually dissolve with component (B).

18. The oral composition of claim 15, wherein component (C) is selected from the group consisting of propylene glycol, glycerol, sorbitol, xylitol and mixtures thereof.

19. The oral composition of claim 14, further comprising at least one additive selected from the group consisting of an abrasive, a binder, a humectant, a surfactant, a flavor, a pH regulator and mixtures thereof.

20. The oral composition of claim 14, wherein said component (A) and said component (B) are present in a ratio of from 8:2 to 1:1.

21. The oral composition of claim 14, wherein said component (A) and said component (B) are present in a ratio of 1:1.

* * * * *